United States Patent [19]

Kezes et al.

[11] Patent Number: 4,803,998
[45] Date of Patent: Feb. 14, 1989

[54] SWAB RETAINING VIAL CAP AND METHOD OF USE

[75] Inventors: C. Albert Kezes, Toronto; F. Walter Schmidt, Oakville; Amsey Buehler, Cobourg, all of Canada

[73] Assignee: NCS Diagnostics, Inc., Mississauga, Canada

[21] Appl. No.: 822,766

[22] Filed: Jan. 27, 1986

[51] Int. Cl.⁴ .............................................. A61B 10/00
[52] U.S. Cl. ....................................... 128/759; 604/1; 435/295
[58] Field of Search ................................ 128/749–759; 220/304; 604/1; 206/209; 435/295

[56] References Cited

U.S. PATENT DOCUMENTS

| | | | |
|---|---|---|---|
| 2,835,246 | 5/1958 | Boettger | 128/759 |
| 3,368,549 | 2/1968 | Barr et al. | 128/759 |
| 3,788,510 | 1/1974 | Collins | 220/304 |
| 3,815,580 | 6/1974 | Oster | 604/1 |
| 3,890,204 | 1/1975 | Avery | 128/759 |
| 4,014,746 | 3/1977 | Greenspan | 128/759 |
| 4,150,950 | 4/1979 | Takeguchi et al. | 128/759 |
| 4,175,008 | 11/1979 | White | 128/759 |
| 4,223,093 | 9/1980 | Newman et al. | 128/759 |
| 4,311,792 | 1/1982 | Avery | 435/295 |
| 4,312,950 | 1/1982 | Snyder et al. | 128/759 |
| 4,353,868 | 10/1982 | Joslin et al. | 128/759 |
| 4,586,604 | 5/1986 | Alter | 128/756 |

FOREIGN PATENT DOCUMENTS 990020 6/1976 United Kingdom ............... 128/759

Primary Examiner—Max Hindenburg
Attorney, Agent, or Firm—Krass & Young

[57] ABSTRACT

A combination of a special swab applicator, a containment vial therefor and a cap for the vial is provided. An elongate vial containing a culture preserving media has one open end and a closed end and threads about its circumference at the open end. The cap has a threaded rim for attachment to the vial and a central section closing off the area inside the rim. The central section has an axially extending bore portion that snuggly fits an end of the swab applicator. The swab applicator has a long shaft with a first section having a length corresponding approximately to the length of the vial and a second section joined to the first by a frangible joint. After use of the applicator it is inserted into the vial and the second section is broken off. The cap is then threaded onto the vial to seal it and capture the first section.

12 Claims, 3 Drawing Sheets

__4,803,998__

SWAB RETAINING VIAL CAP AND METHOD OF USE

BACKGROUND OF THE INVENTION

This invention relates to testing swabs and storage or transport vials therefor and to a method of taking a culture sample.

It is a common practice to use swab applicators to obtain culture samples or samples of a similar nature. Commonly, the applicator has an elongate shaft made of wood or a plastics material. At one end of the shaft is a cotton or synthetic swab. Such applicators may be kept in a sterile package until they are to be used.

For diagnostic and other medical purposes, it is known to provide a sealed transport or storage vial containing a culture preserving substance. The vial is sealed at one end by a removable cap or plug and the interior of and the contents of the vial are sterile. In order to carry out a diagnostic test on a patient, the applicator is used to obtain a culture sample from the area to be tested, for example the patient's throat. After removal of the cap or plug from the vial, the applicator is then placed into the open end of the vial. The open end of the vial is then sealed with the cap. The vial is then transported to the laboratory where the contents thereof are tested.

A potential difficulty with this known system for taking a culture sample test is that it is possible for the doctor or nurse who takes the test to contaminate the test sample by the handling of the swab applicator. Furthermore, because it is necessary for a technician to handle the applicator again when the vial has reached the testing laboratory, further contamination can occur in the laboratory unless the vial and the contents thereof are handled with care. The lab technician could himself be contaminated by his handling of the swab applicator or by touching the inside of the vial.

The present invention seeks to alleviate some or all of the aforementioned problems with known systems. There is disclosed herein a special swab applicator wherein the portion of the applicator that is actually handled by the nurse or doctor taking the test is not inserted in or transported in the vial. Thus the chances of the culture sample being contaminated by the doctor or nurse are decreased. A special vial cap is also provided herein, which cap is able to capture the section of the applicator that is placed in the transport vial. The use of such a cap avoids the need for the lab technician to touch or handle the bottom section of the applicator after it has been transported in the vial.

SUMMARY OF THE INVENTION

According to one aspect of the invention, a vial cap for use on a vial includes a cylindrical rim having threads for attaching the cap to the vial. There is also a central section closing off the area inside the rim and having a central, axially-extending bore portion adapted to fit snuggly around one end of a swab applicator. This central bore portion has one open end to receive the end of the applicator. The central section also has means for directing the one end of the applicator into the central bore portion.

Preferably, the directing means is provided by a conical-shaped connecting wall extending outwardly from the open end of the central bore portion.

According to another aspect of the invention, a combination of a swab applicator, a containment vial therefor, and a cap for the vial includes an elongate vial having one open end and a closed end. This vial has threads about its circumference at the open end and is of a predetermined interior length. A cap for the vial has a threaded rim for attachment to the vial and a central section closing the area inside the rim. The central section has a central, axially-extending bore portion adapted to fit snuggly around an end of a swab applicator and to capture same. The swab applicator has a long shaft and swab material at one end of the shaft. The shaft has a first section having a length corresponding approximately to the predetermined interior length of the vial and a second section joined to the first section by a frangible joint. After use of the swab applicator to obtain a culture sample, the applicator is inserted into the open end of the vial so that the first section is contained in the vial. The second section is then broken off by the user and the cap is threaded onto the vial to seal the vial and capture one end of the first section of the applicator.

According to a further aspect of the invention, there is provided a method of taking a culture sample with a swab applicator and a vial with a cap. The applicator is applied to an area or substance to obtain a culture sample on one end of the applicator. The cap is removed from the vial which may contain a culture preserving media and the sampling end of the applicator is inserted into the vial. An upper section of the applicator is then broken off from a lower section thereof that is substantially contained in the vial. The cap is then replaced onto the vial so as to effect a sealing engagement between the cap and the vial and so as to capture an end of the lower section in the cap.

In the preferred method, the upper section is broken off at a frangible joint pre-formed between the upper and lower sections.

Further features and advantages will become apparent from the following detailed description of a preferred embodiment when considered in conjunction with the accompanying drawings.

DETAILED DESCRIPTION OF PREFERRED EMBODIMENT

Figure 1:
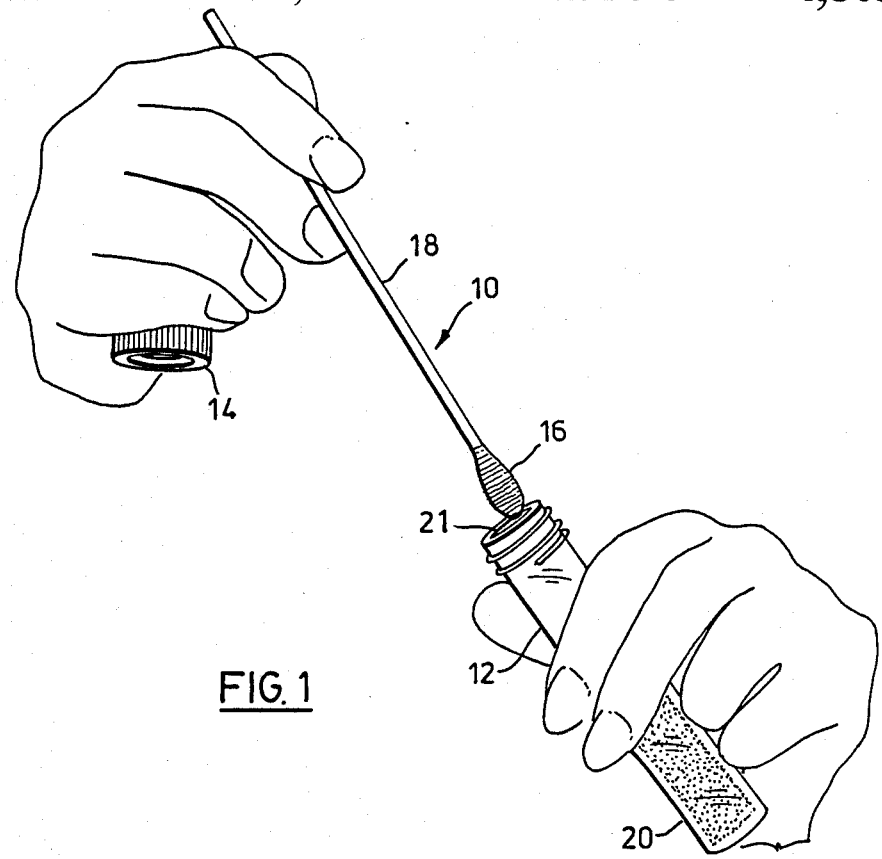
FIG. 1 is an illustration showing how a swab applicator and transport vial constructed in accordance with the invention are used.
Figure 2:
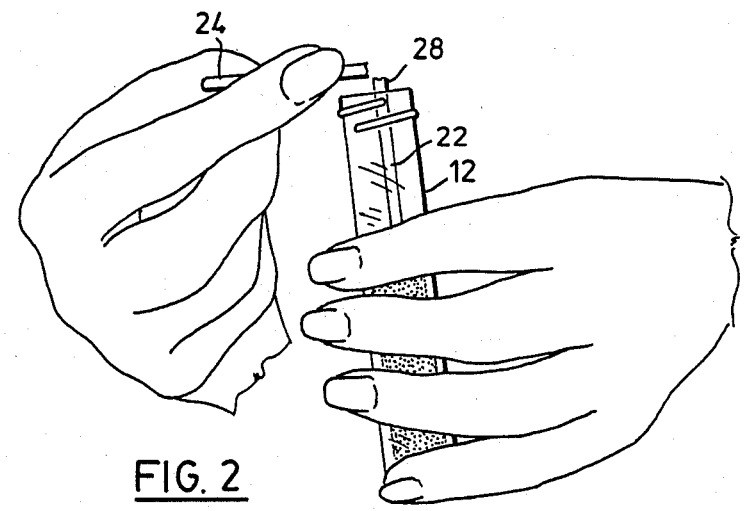
FIG. 2 is a further illustration showing how the swab applicator can be broken off after it is inserted into the vial.
Figure 3:
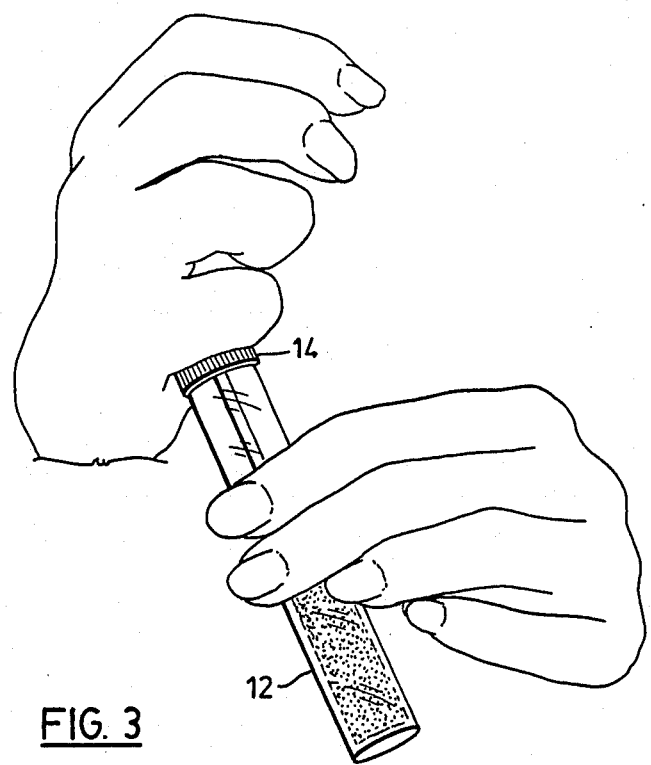
FIG. 3 is an illustration showing how a cap constructed in accordance with the present invention can be reattached to the vial.

FIGS. 1 to 3 illustrate how the combination of a swab applicator 10, a containment vial 12 therefor, and a cap 14 for the vial constructed in accordance with the invention can be used by a doctor or nurse or other person taking a culture sample. In accordance with the standard procedure for a test of this nature. The swab applicator 10 is applied to the area or substance to be tested by rubbing the swab material 16, which may be cotton or a synthetic material, over the area or substance. The long shaft 18 is employed both to reach difficult to reach areas such as the throat and to prevent contact between the hands of the nurse or doctor and the area or material being tested. After the culture sample has been taken, it is known to place the swab applicator in a vial for transport or storage. If necessary or desirable, the vial can contain a culture preserving substance 20 which keeps the culture, if any, alive in the vial but does not permit it to grow. The vial could also be empty. After the known swab applicator has been placed in the vial, the open end 21 of the vial is sealed with a cap or plug. The sealed vial is then brought to a laboratory or other testing area where the nature of the bacteria, virus or microorganism obtained is determined if possible.

Figure 4:
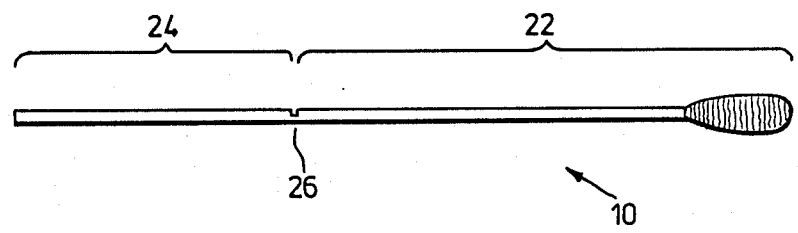
FIG. 4 is a side view of a swab applicator for use in the combination of the invention.

The method of taking a culture sample according to the present invention differs from the aforementioned known procedure in several ways. After the culture sample has been taken with the applicator, the construction of which is shown in detail in FIG. 4, only a lower section 22 of the applicator is actually inserted into the vial. This is because the swab applicator 10 is considerably longer than the length of the vial. The applicator has an upper section 24 which is the portion that is actually handled by the nurse or doctor taking the test. The nurse or doctor should avoid handling or touching in any way the lower section 22 in order to avoid possible contamination thereof. A frangible joint 26 is preformed during the manufacturing of the applicator between the upper and lower sections. This weak or frangible joint can be created by a small knife cut that slightly reduces the cross-section of the shaft. After the lower section of the applicator has been placed in the vial, it is simple for the nurse or doctor to break off the upper section 24 as shown in FIG. 2. The section 24 can then be disposed of since it is no longer required. It should be noted that in the preferred embodiment shown in FIG. 2 the lower section 22 projects slightly from the top of the vial, thus the length of the lower section 22 is slightly greater than the vial chamber. The slight projection 28 is advantagous for reasons that will become apparent hereinafter. After the upper section has been removed, the vial cap 14 is replaced onto the vial in the manner shown in FIG. 3. Because of the construction of the cap and the vial, there is a double seal between them and, in addition, the upper end of the lower section 22 of the applicator is captured in the cap 14. Accordingly, when the vial reaches the laboratory for testing, the applicator can easily be removed from the vial by removal of the cap to which the applicator is now attached.

Figure 5:
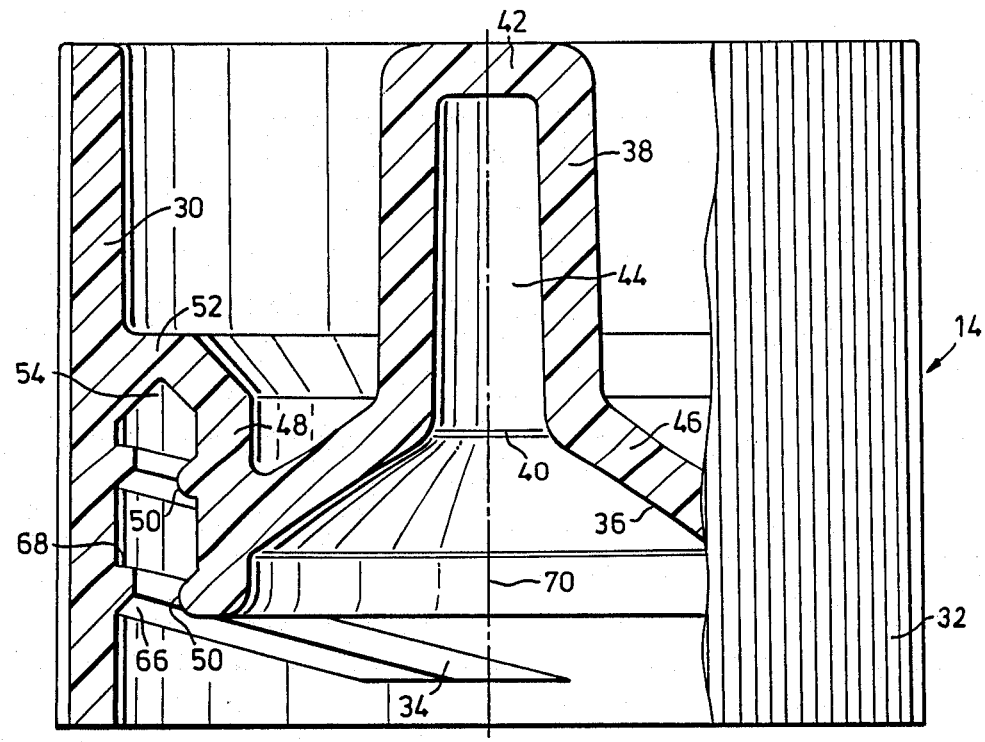
FIG. 5 is a side view, partially in cross-section, illustrating a preferred form of vial cap.

The construction of the special vial cap 14 will now be described with reference to FIG. 5. It is preferably made of soft plastic such as low density polyethylene (food grade) which makes it reasonably flexible. The cap has a generally cylindrical rim 30 that extends the full height of the cap and that preferably has serrations 32 on its outside surface so that it can be grasped easily in a user's fingers. In the preferred embodiment shown, a lower portion of the rim has threads 34 on the inside surface thereof. In one preferred embodiment, the threads have a triple start and are of the right hand type. The thread lead in this embodiment is 0.2389 inch and the thread pitch is 0.0796 inch. The cap has a central section 36 closing the area inside the rim. This section has a central, axially-extending bore portion 38 adapted to fit snuggly around one end of the broken swab applicator 10. This bore portion has one open end 40 to receive the end of the applicator and an upper, closed end 42. In the preferred embodiment shown, the bore 44 tapers slightly inwardly from bottom to top. Thus, as the end of the applicator enters the bore 44, the grip of the cap on the applicator gradually increases becoming quite strong as the end of the applicator reaches the closed end 42.

The central section of the cap also has means for directing the upper end of the lower section 22 of the applicator into the central bore portion. In the illustrated preferred embodiment the directing means comprises a conical-shaped connecting wall 46 extending outwardly from the open end 40 of the central bore portion. In the illustrated embodiment, the inner surface of the connecting wall 46 slopes at an angle of approximately 55° to the central axis of the cap. It will thus be seen that even if the upper end of the applicator after the breaking step is not located on the center axis of the vial, the cap attachment process will eventually push or force the end of the applicator towards the center axis of the vial and into the bore 44.

The central section of the cap further includes an inner cylindrical rim 48 spaced radially inwardly from the rim 30. When the cap 14 is fully attached to the vial, the rim 48 extends along the inside surface of the vial. As shown in FIG. 5, the connecting wall 46 is integrally connected to the rim 48 at a point approximately midway up the height of the rim. Sealing means are preferably formed on the radially exterior surface of the rim 48 for engaging the inside surface of the vial. Preferably these sealing means take the form of two rounded annular protruberances 50 extending outwardly from the rim. These protruberances, which are made from the same plastics material as the cap, act in a manner somewhat similar to O-rings to form a seal between the cap and the vial. The inner rim 48 is connected to the outer rim by a short, radially extending connecting shoulder 52 that extends the entire circumference of the cap. Formed in the bottom of this shoulder is an annular V-shaped groove 54 into which the top end 56 of the vial is pressed for an additional seal between the vial and the cap.

Figure 6:
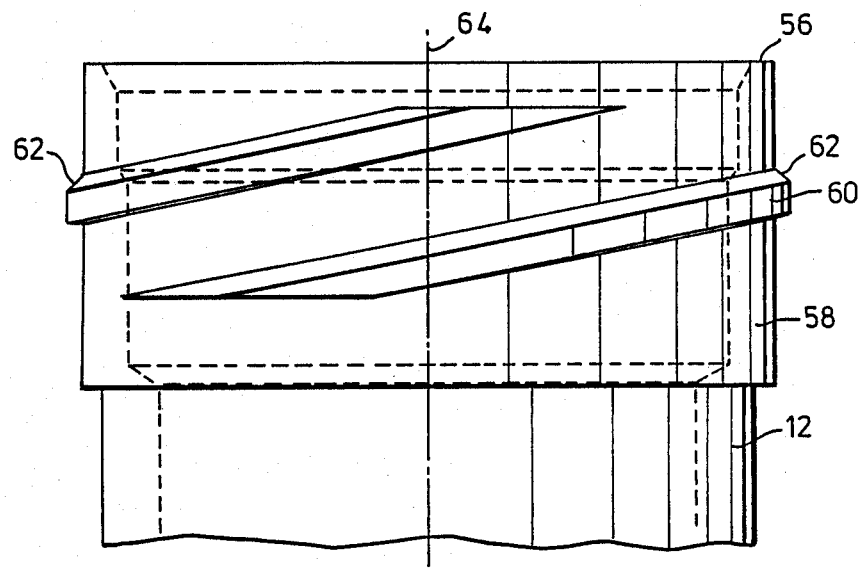
FIG. 6 is a side view of the upper end of a transport vial for use with the cap of FIG. 5.

Turning now to the construction of the vial itself, the upper portion of a preferred form of vial is shown in FIG. 6. The vial 12 which preferably is made of a rigid clear or transparent or translucent plastic has a widened top portion 58 and an open top. The preferred plastics material is crystal styrene (food grade). Formed on the outer surface of the top portion are suitable threads 60 constructed to cooperate and engage the threads of the cap 14. Preferably the threads have a triple start and are right-hand. Preferably the threads on the vial have a sloping top surface 62. This sloping surface together with the sloping surfaces of the threads 34 of the cap permit the cap 14 to be simply pushed by force onto the top of the vial, if desired. Thus, the threads 34 will slide over the threads 62 upon application of sufficient force without damage thereto. In one preferred embodiment of the vial, the sloping surface 62 extends at approximately 45° to the center axis 64 of the vial. As shown in FIG. 5, the threads 34 have a steeply sloped lower surface 66 and an upper surface 68 with a more gradual slope. In a preferred embodiment, the lower surface 66 extends at an angle of approximately 45° to the center axis 70 of the cap. The slope of the upper surface 68 can be 7 to 8° relative to the bottom of the cap.

It will thus be seen that a new vial cap has been provided by this invention, which cap is able to capture one end of a suitable swab applicator so that the swab applicator need not be touched or handled after it has been placed in a transport vial. A preferred form of this cap can either be screwed onto the vial or applied thereto simply by pushing the cap down onto the vial. In addition to seizing the end of the swab applicator in the vial, the cap is able to seal the vial effectively so that the contents thereof cannot become contaminated or contaminate the surrounding area.

It will be appreciated by those skilled in this art that various modifications and changes can be made to the illustrated and described vial, vial cap and swab applicator without departing from the spirit and scope of this invention. Accordingly, all such modifications and changes as fall within the scope of the appended claims are meant to be part of this invention.

We therefore claim:

1. A combination of a swab applicator, a containment vial therefor, and a cap for said vial comprising:
    an elongate vial having one open end and a closed end;
    a cap for said vial having a rim for attachment of said cap to said vial and a central section closing the area inside said rim, said central section having a central, axially extending bore portion adapted to fit capture and retain same;
    and a swab applicator having a long shaft and swab material at one end of said shaft, said shaft having a first section having a length corresponding approximately to the inside length of the vial and a second section joined to said first section by a frangible joint;
    wherein after use of said swab applicator to obtain a culture sample, said swab applicator can be inserted into the open end of the vial so that said first section is contained in said vial, said second section can be broken off by the user, and said cap can be attached to said vial to seal said vial and capture and retain one end of said first section of the applicator.

2. A combination according to claim 1 wherein the central section of said cap has conical-shaped means for directing said one end of said first section into said central bore portion.

3. A combination according to claim 2 wherein said directing means is a conical-shaped wall extending outwardly from an open end of said central bore portion.

4. A combination according to claim 2 wherein the frangible joint in the applicator is formed by a cut in said shaft that reduces the cross-section thereof at said joint.

5. A combination according to claim 2 wherein said cap is provided with sealing means for sealing the connection between said cap and said vial.

6. A combination according to claim 5 wherein said cap includes an inner cylindrical rim spaced radially inwardly from the first mentioned rim and said sealing means are formed on the radially exterior surface of said inner rim.

7. A combination according to claim 6 wherein said sealing means are rounded annular protruberances extending outwardly from said inner rim.

8. A method of taking a culture sample with a swab applicator and a vial having a cap equipped with means for capturing and retaining a section of said applicator comprising:
    applying said applicator to an area or substance to obtain a culture sample on one end of said applicator;
    inserting said one end of the applicator into said vial which has an open top;
    breaking off an upper section of said applicator from a lower section thereof that is substantially contained in said vial, and
    attaching said cap to the top of said vial so as to effect a sealing engagement between said cap and said vial and so as to capture and retain an end of said lower section in said cap.

9. A method according to claim 8 wherein said upper section is broken off at a frangible joint preformed between the upper and lower sections.

10. A method according to claim 9 wherein said cap is attached to said vial by cooperating threads formed on said cap and on said vial.

11. A method according to claim 10 wherein said end of the lower section is captured by insertion of the end into a central, axially-extending bore portion of said cap, a friction fit being created between the inner surface of said bore portion and said lower section of the applicator.

12. A method according to claim 9 wherein only the upper section of said applicator is touched by the user during the sample taking and the breaking step.

* * * * *